United States Patent [19]
Ryan

[11] Patent Number: 5,171,485
[45] Date of Patent: Dec. 15, 1992

[54] SCENT EMITTING DEVICE FOR AUTOMOBILES

[75] Inventor: Roger D. Ryan, 1801 W. Tichenor St., Compton, Calif. 90220

[73] Assignee: Roger D. Ryan, Compton, Calif.

[21] Appl. No.: 770,905

[22] Filed: Oct. 4, 1991

[51] Int. Cl.⁵ ............................................. B01F 3/04
[52] U.S. Cl. ................................. 261/27; 261/99; 261/72.1; 261/DIG. 65; 422/124
[58] Field of Search ............... 239/44; 261/27, 72.1, 261/99, DIG. 65; 422/124

[56] References Cited

U.S. PATENT DOCUMENTS

| | | | |
|---|---|---|---|
| 3,031,146 | 4/1962 | Albamonte | 261/DIG. 65 |
| 3,633,881 | 1/1972 | Yurdin | 239/44 |
| 3,722,182 | 3/1973 | Gilbertson | 261/DIG. 65 |
| 4,078,891 | 3/1978 | Madjar | 261/DIG. 65 |
| 4,339,079 | 7/1982 | Shibagaki | 261/DIG. 65 |
| 4,346,059 | 8/1982 | Spector | 422/124 |
| 4,383,377 | 5/1983 | Crafton | 422/124 |
| 4,601,886 | 7/1986 | Hudgins | 422/124 |
| 4,677,902 | 7/1987 | Takemasa | 422/124 |
| 4,722,264 | 2/1988 | DeGuisseppe | 422/124 |
| 4,805,520 | 2/1989 | Freedman | 422/124 |

FOREIGN PATENT DOCUMENTS

0359984  3/1990  European Pat. Off. .... 261/DIG. 65

Primary Examiner—Tim Miles

[57] ABSTRACT

An ELECTRONIC FRAGRANCE EMITTING SYSTEM FOR MOTORED VEHICLES. The system consists of a plastic reservoir which houses liquid fragrance, and a pump that extracts liquid fragrance from the reservoir and transports it to a holder mounted in the passenger air vent. Action is initiated by a button mounted on the dashboard or console. The precise amount of fragrance extracted is controlled by an event timer mounted under the dashboard. Once fragrance enters holder it is quickly absorbed via a felt pad. AC Heater or vented air entering vehicle cabin will then distribute fresh scent.

4 Claims, 7 Drawing Sheets

SCENT EMITTING DEVICE FOR AUTOMOBILES

WHAT IT RELATES TO

The present invention relates to a system that emits a pleasant aromatic scent.

HOW IT DIFFERS

Fragrant devices producing such a scent have been widely used in homes and in vehicles. This is well known. Unfortunately, some devices scents deplete quickly, thus requiring replacement of the entire device. Others being complicated in structure require the dexterity of a surgeon to refill. Furthermore, they are of the stick-on, hang or variety, and while appearing to be convenient, certain devices cause driver distraction and can actually detract vehicle ergonomics. This system will be integrated within the vehicle (under the hood & beneath dashboard). Activator button used will be of O.E.M. type and will be logically placed.

MY OBJECTIVES

It is the intention of this inventor to provide an operational, virtually trouble free (user need only to refill reservoir, and have felt element replaced around every two year period), integrated Unit within the vehicle that has the capacity to generate a constant fresh scent upon users discretion, while providing an almost infinite life span.

BRIEF SUMMARY

A system in harmony with this invention comprises a plastic molded reservoir—which houses the liquid fragrance, mounted under the hood. Reservoir being semi-transparent—an electric pump of lightweight construction mounted next to reservoir which when engaged (via event timer) transfers a predetermined amount of liquid from reservoir to a circular holder mounted inside vehicle passenger vent. Holder houses a felt element which quickly absorbs liquid fragrance—a portion of element being exposed so when air passes through vent—the scent will be emitted into vehicle cabin. All action is initiated via a logically mounted button—(console or dash) which is tied into an event timer mounted under the dash board.

BRIEF DESCRIPTION OF THE DRAWINGS

A preferred embodiment of the invention is described in detail by way of a specific example, with reference to the accompanying drawings; WHEREIN.

DETAILED DESCRIPTION

FIGS. 1-4 comprise the entire (system) of this invention. It includes all parts of the system. Following is a detailed description of FIGS. 5-18 as well as FIGS. 1-4—turn now to the drawings and initially to FIG. 1 which comprises a completely circular holder having a top cap 1 and bottom container (or holder) 2, both pieces being formed out of an injection molded plastic. The top circular cap 1 as well as the bottom holder 2 have a small round opening 3 in its side that allows a thin flexible plastic piece 9 called a filler tube to be inserted. Once the top cap is screwed down, the two holes will line up 3. The top portion of cap 1 has a cut out 32 (FIG. 9) that allows for a square shape piece of felt element 8 to be placed inside of said holder 1 and 2.

Figure 10:
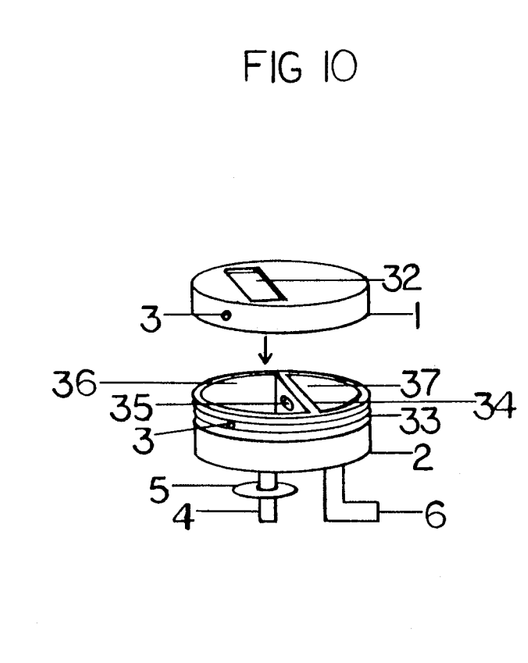
FIG. 10 shows the adjoining top and bottom of holder in perspective.

The bottom half of holder (or container) 2 has threads 33 of FIG. 10 that allow top cap 1 (also having threads) 40 (FIG. 18) to screw on securely. In the holder 2 resides a partition 34. This partition 34 is not an added piece snapped in, but rather formed as one piece with bottom holder 2. During the plastic forming process—this partition, has its wall extend to both sides of the holder, bottom of partition being flush with bottom of holder, and the top of partition being even with top of holder 2 (FIG. 10). This is in effect creating two separate unequal bowls or containers within bottom holder 2. The front or main container 36 making up 75% of entire space. The rear container 37 making up the remaining 25% (FIG. 10). The partition will have a small hole 35 placed near top. This is for safety reasons—should front container unexpectedly rise to unwanted levels all excess liquid france will quickly be drained away into safety side of container 37 and passed on via safety drain line 6. The mounting stem 4 and safety drain line 6 will, like the partition be formed as one piece with bottom holder—through an injection mould process—and are not attached externally by snapping on or glue on means.

Figure 1:
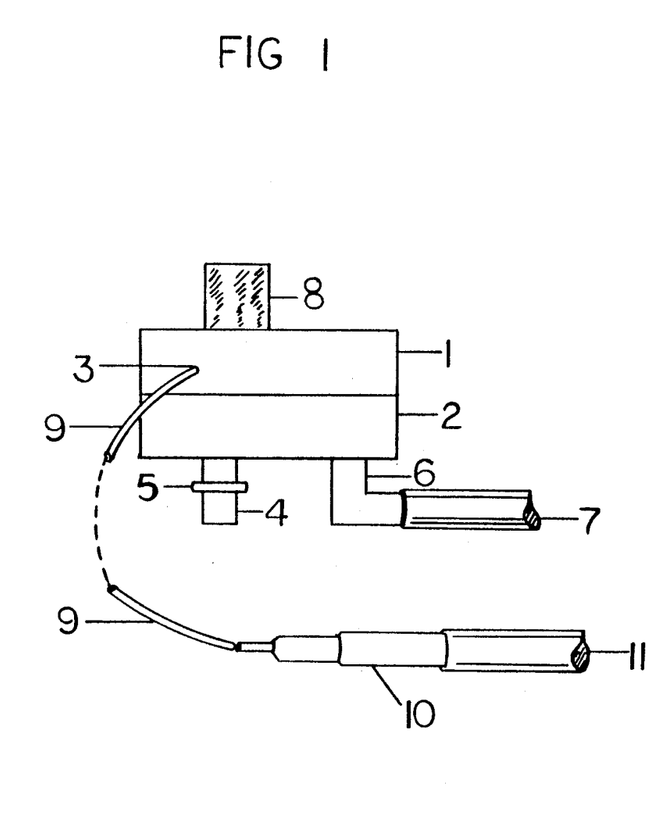
FIG. 1 is a plain view of the right side of a device along with its accompanying filler tube in accordance with this invention.
Figure 2:
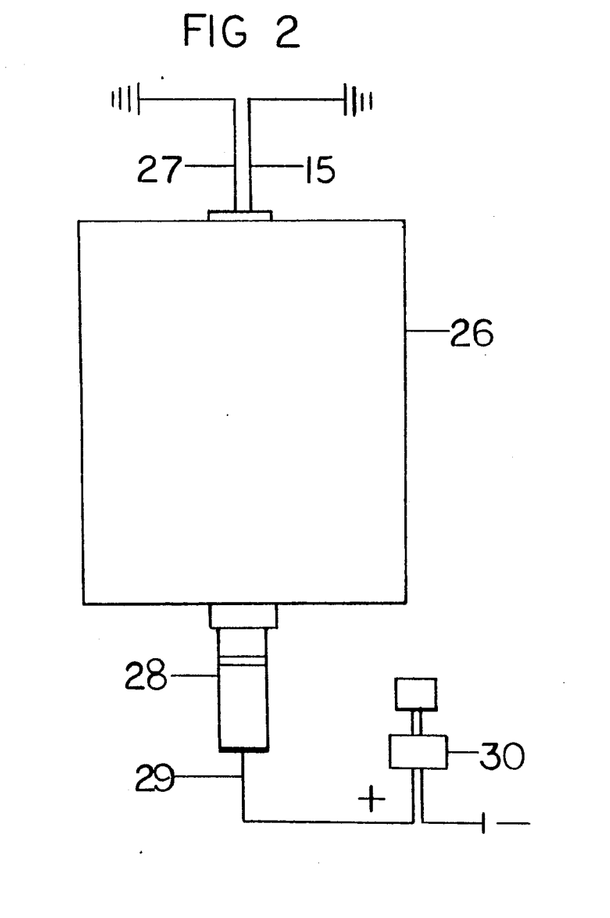
FIG. 2 is a front elevational view of a small encasement housing the electronic components needed for timing—also accompanied by an activation button.
Figure 3:
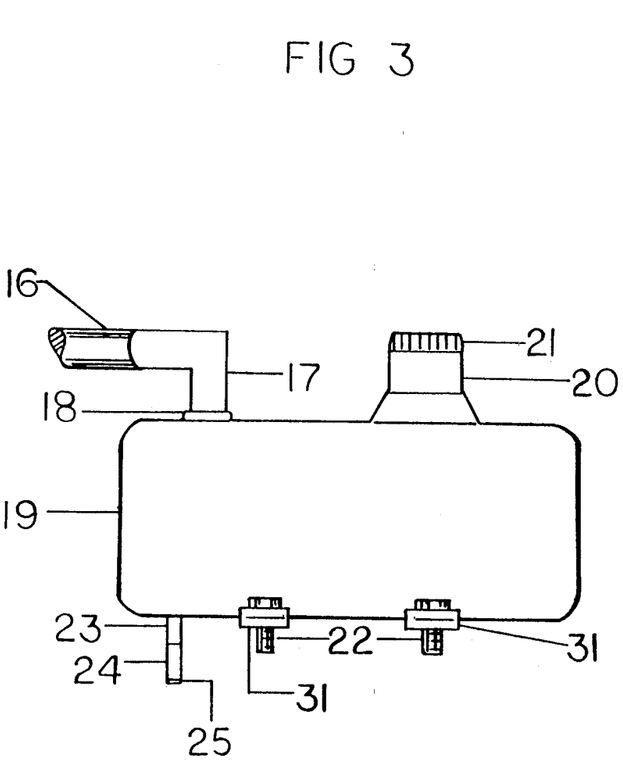
FIG. 3 is a plain frontal view of a plastic reservoir containing its accompanied parts in accordance with this invention.
Figure 4:
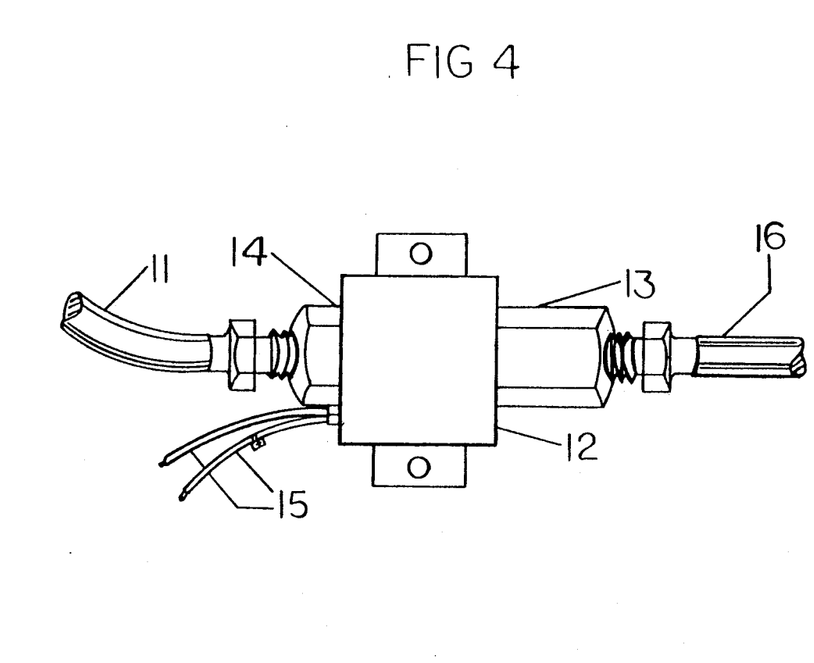
FIG. 4 is a plain frontal view of a pump with its attached rubber lines in accordance with this invention.
Figure 5:
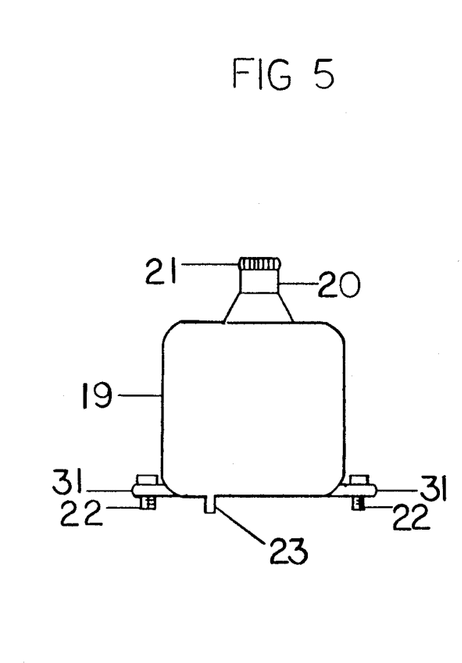
FIG. 5 is a plain view of the right side of reservoir in FIG. 3.
Figures 6, 7:
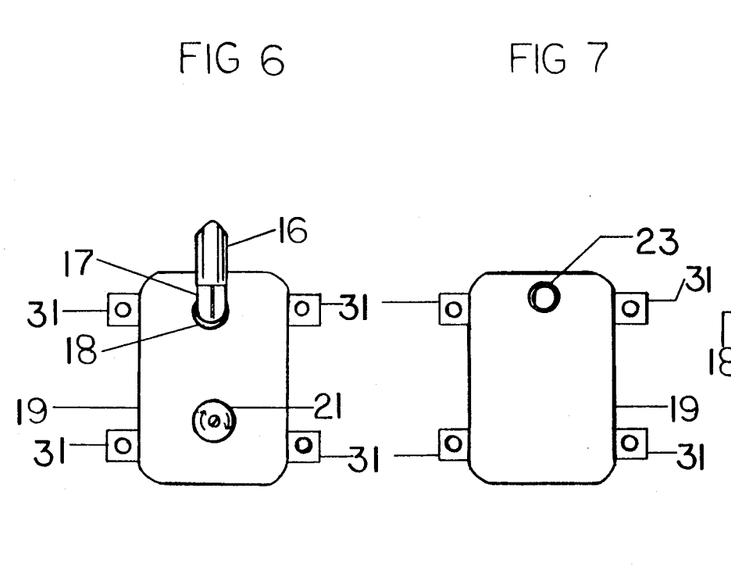
FIG. 6 is a top elevational view of reservoir in FIG. 3.
FIG. 7 is a bottom elevational view of reservoir in FIG. 3.
Figure 8:
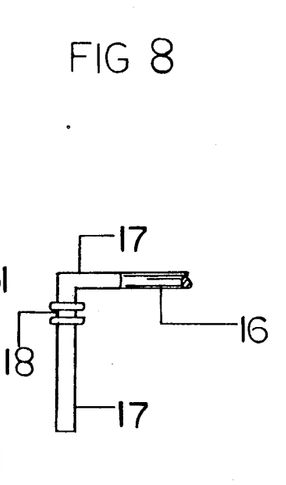
FIG. 8 is a plain view of pick-up tube that mounts in top of reservoir in FIG. 3.
Figure 9:
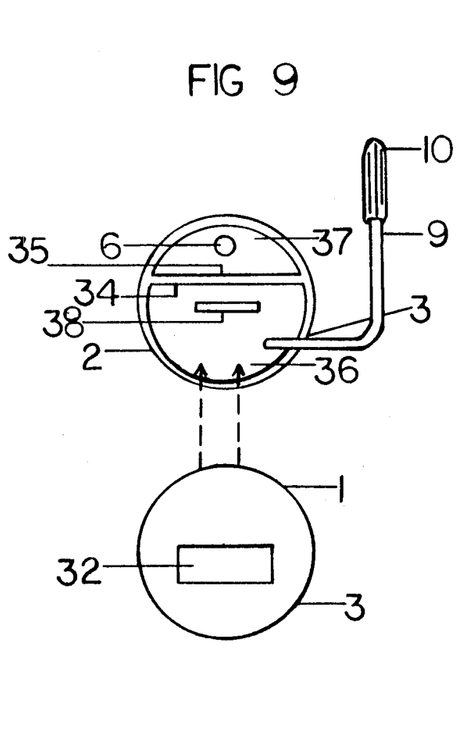
FIG. 9 is a top elevational view of a holder. This view shows the inside of holder with cap removed—also shown is the removed cap—(top view elevated).
Figure 11:
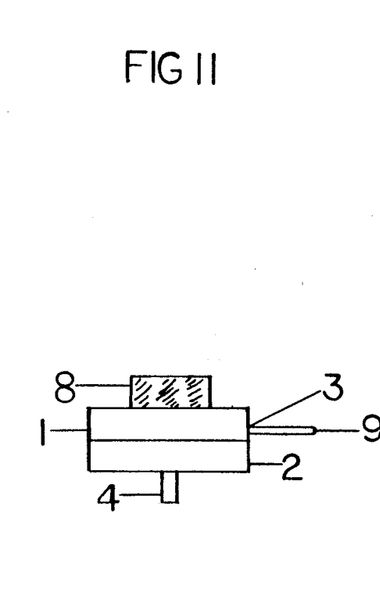
FIG. 11 is a plain front view of holder with the felt element and filler tube in place.
Figure 12:
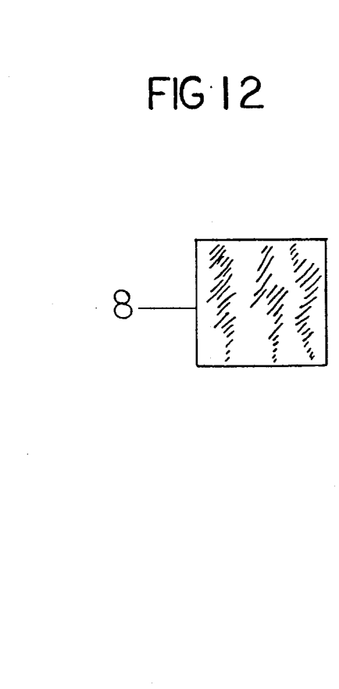
FIGS. 12 and 12A are plain front and side views of felt element which fits inside of holder.
Figures 12A, 13, 14:
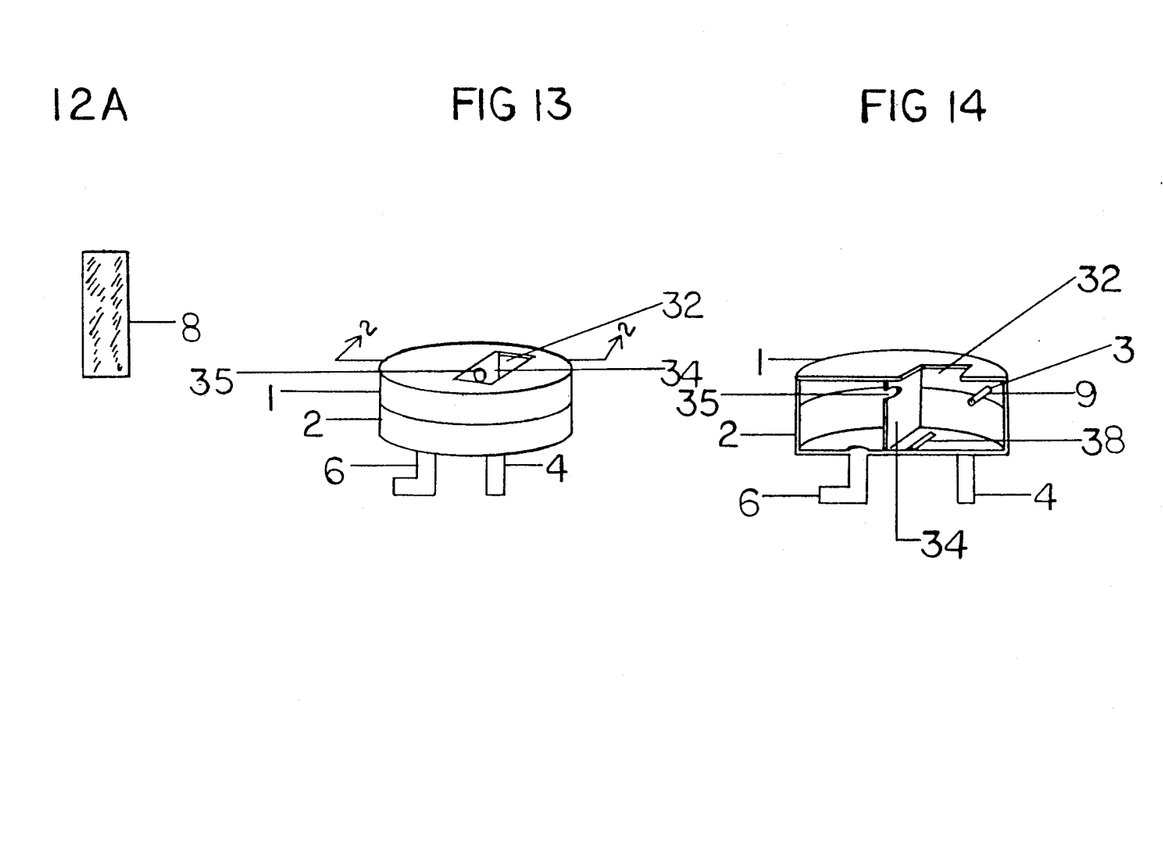
FIG. 13 is a perspective view showing the holder with top piece assembled.
FIG. 14 is a sectional view taken on the line 2—2 of FIG. 13.
Figure 15:
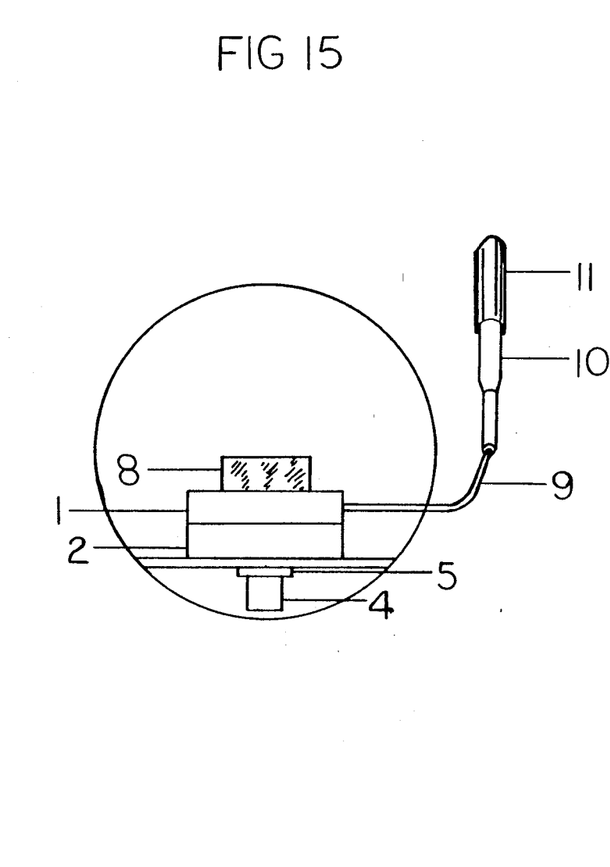
FIG. 15 is a exploded plain frontal view of holder in FIG. 16. This view was included to show relationship of holder and vehicle air vent.
Figure 16:
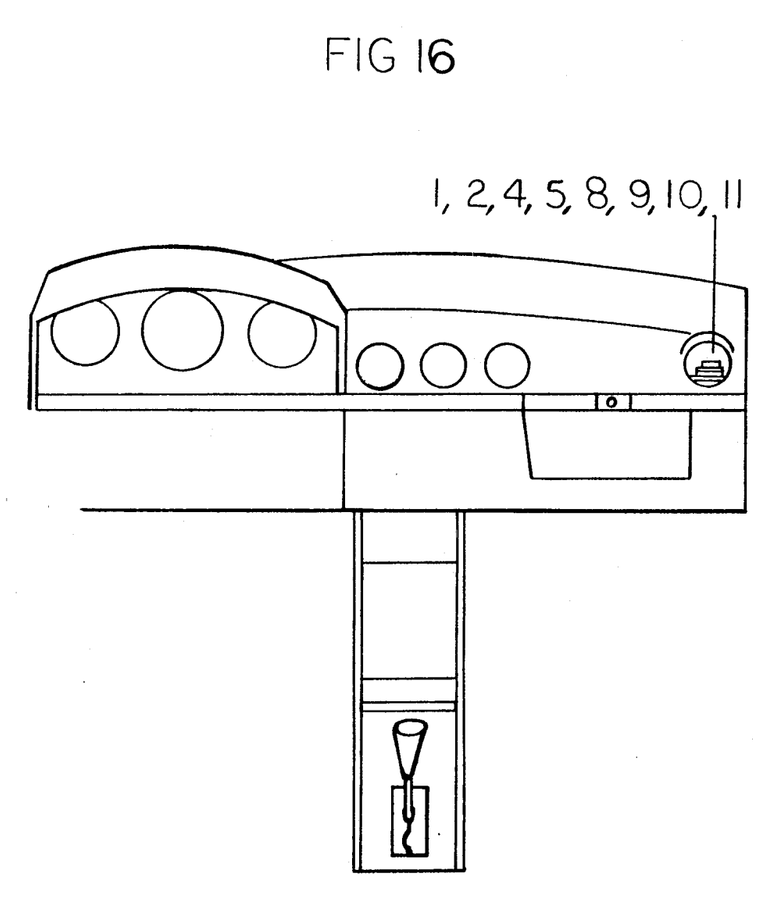
FIG. 16 is a drawing of a typical dashboard of a vehicle. It should be understood that the vehicle dashboard is for illustrative purposes only and is not claimed as part of this invention—but rather reveals where holder will mount inside of vehicle. Reference numbers 1,2,4,5,8,9,10, and 11—comprise all pieces that make up holder. This illustration also has the absence of the venetian blind which will be put back into place upon installation of holder.
Figures 17, 18:
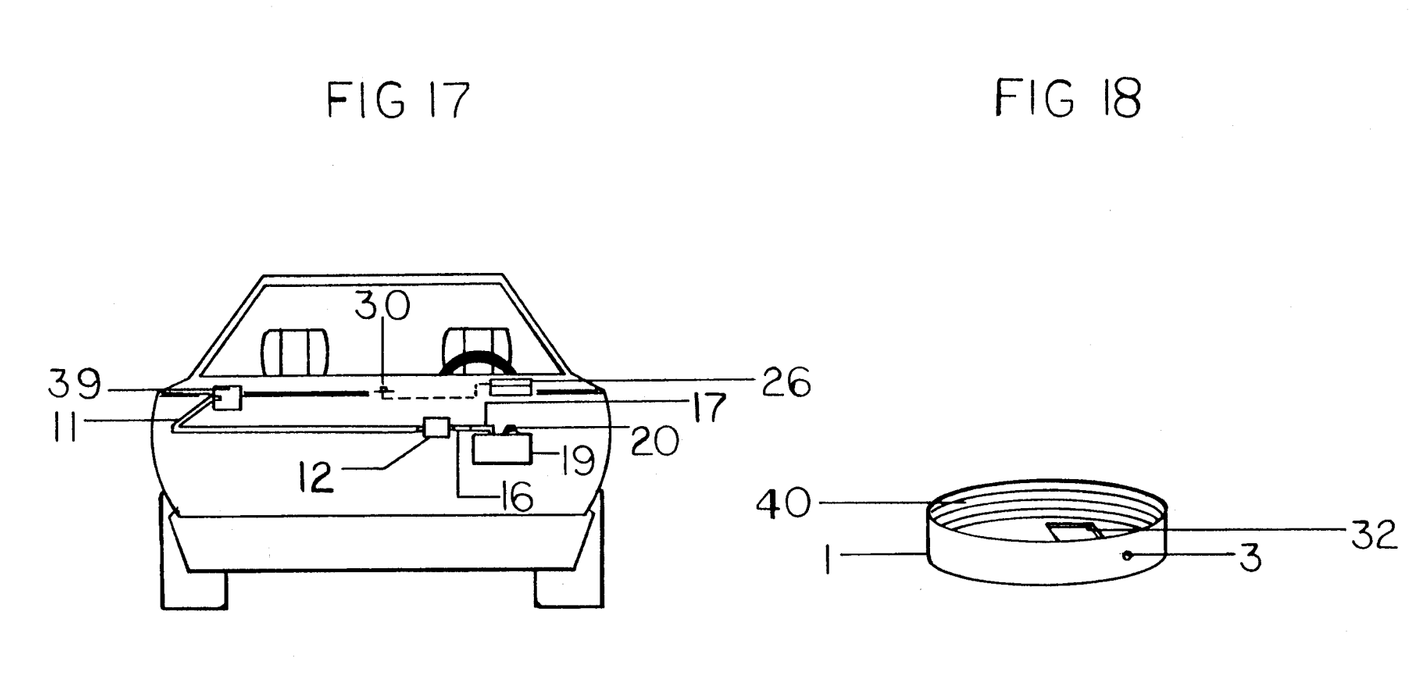
FIG. 17 is a plain frontal view of an automobile—while the automobile is not a part of this invention, and is used for illustrative purposes only, it does show the parts of the system and how they integrate with the vehicle.
FIG. 18 is an elevated semi-exploded view of inner side of top cap with threads showing.

As was stated the drain lines purpose is to prevent overflow of the system. Its round opening 6 of FIG. 9 will be of sufficient means. The drain line 6 (FIG. 1) will attach to a rubber hose 7 (FIG. 1) that will allow excess liquid to be redirected back to reservoir 19 (FIG. 3). The felt element 8, made of an absorbent material, will sit flush on the floor of bottom container 2 in front of partition 34 on larger side of holder 36 (FIG. 10) having only a portion of element extruding from top cap 1 (FIG. 11). The stabilizer 38 (FIGS. 9 and 14) will keep element 8 stable. It (stabilizer 38) is only a slight rise or indention which is formed during the injection process. The device (holder) will be kept secure in the vehicle vent dual via a pal nut 5 (FIG. 10) that slips over mounting stem 4. Two small holes are made in the air duct floor to allow mounting stem 4 and drain line 6 access to mount. Bottom of holder 2 fits flush with the bottom of the air duct (FIG. 15). A small incision is placed in the side of the air duct to allow thin plastic filler tube 9 access to the holder (FIG. 15). The filler tube is inserted into a small hole on holder 3 (FIG. 1). Once button 30 (FIG. 2) is engaged, liquid fragrance is transferred to holder 2 via filler tube 9, the adapter 10 (FIG. 1) allows the smaller filler tube 9 to connect to larger hose 11 (FIG. 1)(Adapter and Filler Tube both formed of a plastic construction). The rubber hose 11 (FIG. 1) used is installed along the passenger side of the vehicle (FIG. 17)(most cases) and a small hole or opening is made in the fire wall of the vehicle to allow the hose access to the passenger cabin, and more specific to passenger air vent 39 (FIG. 17) where the holder resides (FIG. 15 and 16), the opposite end of the hose being attached to outlet end 14 of an electric pump (FIG. 4) mounted under the hood of the vehicle next to reservoir 19, the inlet side of pump 13 also having a hose 16 attached will connect to pick-up tube 17 of FIGS. 3-8 that is mounted inside of plastic rectangular shape reservoir 19 (FIG. 3). Reservoir 19 houses liquid fragrance until small measured amounts are called upon and transferred to the holder in the cabin of the vehicle. The pick-up tube 17 is responsible for picking up (drawing) liquid out of reservoir 19 via pump 12 (FIG. 4). Both reservoir and pick-up tube will be made of a plastic semi-transparent material—so fluid levels can be easily monitored—pick-up tube will have a rubber grommet 18, that can be slid up its shaft 17 (FIG. 8). Its job is to keep the pick-up tube securely mounted inside of the hole in reservoir 19. The bottom side of the reservoir (FIG. 7) shows drain plug 23. The rubber hose 24 (FIG. 3) is flexible and permits user ability to drain reservoir 19 of contents should user desire to switch scents before—running out. The cap 25 (FIG. 3) is easily removed and reapplied. The reservoir has extrusions 31 (FIGS. 6-7) and mounting screws 22 allowing it to be mounted to a support bracket. Reservoir can be easily filled by unscrewing cap 21 (FIG. 6) adding liquid fragrance and replacing cap. All action is initiated via a button 30 (FIG. 2) mounted in a logical position. Button will be tied into a brain (black box) 26 (FIG. 2) mounted beneath the dashboard (FIG. 17). Its contents will contain an event timer that controls the amount of time pump 12 (FIG. 4) will run. Time can be varied to compensate for different hose lengths, position of holder etc. (Variations made internally by installer and not by the user of the system). Black box 26 has three separate lines out—all lines will be of an RCA type. The RCA plug is used for ease of maintenance—should event timer require it. You would simply slip RCA plug out, thus leaving activation button mounted intact. Along with the other two lines—one other to pump 12 (FIG. 4) and the last being tied into the battery giving unit its needed current.

OPERATION OF SYSTEM

Only a predetermined amount of liquid fragrant will be emitted upon engagement of activator button 30. Button must be re-engaged in order to repeat process—the precise amount transferred to holder 2 is gradually absorbed by felt element 8. Scent is then released throughout vehicle cabin. Venetian blinds, and/or air condition & heating speed controls will regulate scent distribution and intensity. The holder 1-2 has been so designed as to minimize unnecessary air flow restrictions. The circular shape allows unrestricted air passage around its body. The felt element 8 being fairly square shape in design insures the trapped scent will be picked up by the passing air. Variations and modifications are possible without departing from the spirit of the invention.

What is claimed is:

1. A scent-emitting Electronic Aromatic Device comprising a reservoir used to house a liquid fragrant, an electric pump used to extract said liquid fragrant, an event timer used to control said electric pump and a holder (container), said reservoir being semi-transparent so liquid levels can be monitored, said reservoir further having a plastic screw-on type cap for filling and refilling of liquid contents, said reservoir further having a small hole in its top section making provisions for a pick-up tube to be inserted, said tube providing extraction means of said liquid fragrant via said electric pump, said pick-up tube having a rubber part placed along its shaft and being inserted in said hole of said reservoir, thus securing said pick-up tube in its place, said reservoir further having a nipple with a rubber hose attached along the bottom of said reservoir, said nipple and said rubber hose providing a means for drainage of said liquid contents, said reservoir also having extrusions along its sides creating a means for said reservoir to be mounted with a bracket.

2. A scent emitting Electronic Aromatic Device according claim 1 wherein said pump is of a light weight construction, and further having the ability to extract a liquid fragrant from said reservoir and transfer it to a specific destination, said pump being controlled by said event timer.

3. A scent emitting Electronic Aromatic Device according to claim 1 wherein said container (holder), has a top cap and a bottom holder adapted to receive a pre-determined amount of liquid fragrant, said bottom holder (container) being circular in shape and having a partition therein, thus forming two completely separate containers, the front portion being considerably larger than the rear portion, said partition having a circular hole cut-out near its top, thus providing a safety exit of liquid fragrant should said front portion of container start to fill over, said holder further having threads so said top cap can securely screw onto said bottom portion of said holder, said top cap further providing a cut-out so an absorbent material can be placed in said container, said top and bottom holder further having a small hole in its sides, thus allowing a thin plastic filler tube to be inserted, said tube providing a means for a liquid fragrant to enter said holder via aforementioned electric pump, said holder further having two small stems extruding from beneath said bottom portion of holder, one in front, providing a means for mounting entire said holder into vehicle's air vent, the second, or rear stem being hollow is in effect a safety drain line, eliminating any excess liquid fragrant said front holder is unable to contain.

4. A scent-emitting Electronic Aromatic Device according to claim 1 wherein said timer regulates the precise duration of time said electric pump will operate, said timer responding to the engagement of a logically placed button within the cabin of the vehicle.

* * * * *